(12) United States Patent
Arnal

(10) Patent No.: US 7,947,047 B2
(45) Date of Patent: May 24, 2011

(54) MEDICAL SCREWDRIVERS AND METHODS

(75) Inventor: Kevin R. Arnal, Excelsior, MN (US)

(73) Assignee: AMS Research Corporation, Minnetonka, MN (US)

( * ) Notice: Subject to any disclaimer, the term of this patent is extended or adjusted under 35 U.S.C. 154(b) by 197 days.

(21) Appl. No.: 11/156,915

(22) Filed: Jun. 20, 2005

(65) Prior Publication Data
US 2007/0005076 A1    Jan. 4, 2007

(51) Int. Cl.
A61B 17/58 (2006.01)
(52) U.S. Cl. .......................... 606/104; 81/60
(58) Field of Classification Search .................. 606/104, 606/86 R, 86 A, 86 B, 99, 279; 81/60–63
See application file for complete search history.

(56) References Cited

U.S. PATENT DOCUMENTS

| | | |
|---|---|---|
| 3,973,605 A | 8/1976 | DeCarp |
| 4,078,589 A | 3/1978 | Miller |
| 4,243,212 A * | 1/1981 | Bunyea et al. .................. 269/75 |
| 4,549,538 A | 10/1985 | Schadrack et al. |
| 4,632,100 A | 12/1986 | Somers et al. |
| 4,941,466 A | 7/1990 | Romano |
| 5,002,546 A | 3/1991 | Romano |
| 5,142,954 A | 9/1992 | Starke |
| 5,354,298 A | 10/1994 | Lee et al. |
| 5,364,408 A | 11/1994 | Gordon |
| 5,464,407 A | 11/1995 | McGuire |
| 5,520,700 A | 5/1996 | Beyar et al. |
| 5,584,860 A | 12/1996 | Goble et al. |
| 5,611,515 A | 3/1997 | Benderev et al. |
| 5,628,751 A | 5/1997 | Sander et al. |
| 5,643,320 A | 7/1997 | Lower et al. |
| 5,674,247 A | 10/1997 | Sohn |
| 5,685,204 A * | 11/1997 | Braun .............................. 81/63.1 |
| 5,782,862 A | 7/1998 | Bonutti |
| 5,814,051 A * | 9/1998 | Wenstrom, Jr. ................ 606/104 |

(Continued)

FOREIGN PATENT DOCUMENTS
FR     1072672     9/1954
(Continued)

OTHER PUBLICATIONS

Cespedes et al., Male Slings for Postprostatectomy Incontinence, Techniques in Urology vol. 7, No. 2, pp. 176-183 (2001).

(Continued)

Primary Examiner — Eduardo C Robert
Assistant Examiner — Tara R Carter
(74) Attorney, Agent, or Firm — Kimberly K. Baxter; Gregory L. Koeller

(57) ABSTRACT

The invention provides a medical screwdriver having a sleeve that can be coupled to the medical screwdriver without the need to align the sleeve to the medical screwdriver. The medical screwdriver includes a body portion having a receiver, a drive shaft, a sleeve, and a coupling connecting the sleeve to the receiver. The sleeve surrounds at least a portion of the drive shaft when coupled to the receiver. The coupling comprises an end of the sleeve and the receiver of the body portion. The end of the sleeve and the receiver are designed so that the end of the sleeve can be coupled with the receiver of the body portion without rotationally aligning the end of the sleeve to the receiver of the body portion and so that the sleeve is prevented from rotating in a direction of rotation during use.

29 Claims, 6 Drawing Sheets

U.S. PATENT DOCUMENTS

| | | | |
|---|---|---|---|
| 5,836,314 | A | 11/1998 | Benderev et al. |
| 5,842,478 | A | 12/1998 | Benderev et al. |
| 5,860,425 | A | 1/1999 | Benderev et al. |
| 5,944,724 | A | 8/1999 | Lizardi |
| 5,968,062 | A | 10/1999 | Thomas et al. |
| 5,972,000 | A | 10/1999 | Beyar et al. |
| 6,089,133 | A * | 7/2000 | Liao ................................ 81/438 |
| 6,241,736 | B1 | 6/2001 | Sater et al. |
| 6,264,676 | B1 | 7/2001 | Gellman et al. |
| 6,282,998 | B1 * | 9/2001 | Beach .............................. 81/437 |
| 6,319,272 | B1 * | 11/2001 | Brenneman et al. ........... 606/232 |
| 6,322,492 | B1 | 11/2001 | Kovac |
| 6,328,686 | B1 | 12/2001 | Kovac |
| 6,328,744 | B1 | 12/2001 | Harari et al. |
| 6,334,446 | B1 | 1/2002 | Beyar |
| 6,382,214 | B1 | 5/2002 | Raz et al. |
| 6,387,041 | B1 | 5/2002 | Harari et al. |
| 6,406,480 | B1 | 6/2002 | Beyar et al. |
| 6,423,072 | B1 | 7/2002 | Zappala |
| 6,440,154 | B2 | 8/2002 | Gellman et al. |
| 6,575,984 | B2 | 6/2003 | Beyar |
| 6,575,998 | B2 | 6/2003 | Beyar |
| 6,589,249 | B2 | 7/2003 | Sater et al. |
| 6,592,610 | B2 | 7/2003 | Beyar |
| 6,602,260 | B2 * | 8/2003 | Harari et al. ................... 606/104 |
| 6,635,058 | B2 | 10/2003 | Beyar et al. |
| 6,660,010 | B2 | 12/2003 | Gellman et al. |
| 6,663,642 | B2 | 12/2003 | Beyar et al. |
| 6,746,455 | B2 | 6/2004 | Beyar et al. |
| 6,951,565 | B2 * | 10/2005 | Keane et al. ................... 606/146 |
| 7,089,828 | B1 * | 8/2006 | Ho ..................................... 81/60 |
| 2002/0052630 | A1 * | 5/2002 | Morgan et al. ................. 606/232 |
| 2002/0095181 | A1 | 7/2002 | Beyar |
| 2002/0107562 | A1 * | 8/2002 | Hart et al. ..................... 623/1.15 |
| 2004/0068269 | A1 * | 4/2004 | Bonati et al. ................... 606/104 |
| 2004/0127916 | A1 * | 7/2004 | Bolduc et al. .................. 606/151 |
| 2004/0243139 | A1 * | 12/2004 | Lewis et al. ................... 606/104 |
| 2005/0228400 | A1 * | 10/2005 | Chao et al. ..................... 606/104 |

FOREIGN PATENT DOCUMENTS

| | | |
|---|---|---|
| GB | 2 268 690 A | 7/1993 |

OTHER PUBLICATIONS

Franco et al., Suburethral Sling for Male Urinary Incontinence, Infections in Urology vol. 14 No. 1, 7pages (May/Jun. 2001).

Jacoby et al., Male Sling: A Multicenter Retrospective Analysis, Western Section AUA, pp. 86 (Sep. 2001).

Jacoby et al., Male Sling: A New Perineal Approach, 1 page (Dec. 1999).

Kovac et al., Pubic Bone Suburethral Stabilization Sling: A Long-Term Cure for Sui?, Contemporary OB/GYN, pp. 1-8 (Feb. 1998).

Madjar et al., Bone Anchored Sling for the Treatment of Post-Prostatectomy Incontinence, The Journal of Urology, vol. 165, No. 1, pp. 72-76 (Jan. 2001).

Precision Tack, Transvaginal Anchor System, The Precise Approach to Transvaginal Sling Procedure (advertisement), Boston Scientific Corporation, Microvasive, 4 pages (Jun. 1998).

Precision Twist, Transvaginal Anchor System, Low Profile Design for Precise Anchor Placement (advertisement), Boston Scientific Corporation, Microvasive, 2 pages (2000).

Vesica Sling Kits, Simplifying Sling Procedures, Boston Scientific Microvasive, 4 pages (1998).

Vesica Sling Kits, A New Approach to Bladder Neck Suspension, Boston Scientific Microvasive, 4 pages (1995).

PCT International Search Report for PCT/US2006/023935, mailed Feb. 15, 2007 (4 pages).

* cited by examiner

MEDICAL SCREWDRIVERS AND METHODS

TECHNICAL FIELD

The invention relates to medical screwdrivers such as those used for inserting a medical screw into bone. More particularly, the invention relates to medical screwdrivers that include a sleeve to isolate a drive shaft of the screwdriver from tissue surrounding an implant site.

BACKGROUND

Various conditions are treated by implantation of a medical device secured by a screw, the screw being installed using a screwdriver having a powered rotating shaft.

As an example, urinary incontinence is a condition that occurs in men and women, and that can be treated by installation of a medical implant. In women, urinary incontinence may be caused by urethral hypermobility, a condition in which the bladder neck and proximal urethra may rotate and descend in response to increases in intra-abdominal pressure. Hypermobility can result because of aging, child delivery, or conditions that weaken, stretch, or tear the muscles around the bladder, bladder neck, urethra, or a combination of these. Urinary incontinence can also be caused by intrinsic sphincter deficiency, a condition in which the urethral sphincter does not coapt properly. In males, urinary incontinence may be caused by damage to the urethral sphincter such as can occur after prostatectomy, after radiation treatment, or after pelvic accidents. Other reasons for male incontinence include bladder instability, over-flowing incontinence, and fistulas.

There are numerous approaches for treating urinary incontinence. In a bladder neck suspension procedure for treating hypermobility, sutures are placed around the muscle groups on either side of the urethra and are affixed to the pubic bone or other supporting structures to reposition and resuspend the proximal urethra. Also common are sling type operations, which may be performed to treat urethral hypermobility, intrinsic sphincter deficiency, or both. In a sling type operation, a sling is placed under the urethra and bladder and is tensioned to elevate and stabilize the urethra, prevent excessive downward mobility, or compress the sphincter to treat intrinsic sphincter deficiency.

In these procedures, sutures are anchored to supporting structures such as the pubic bone, Cooper's ligament, or the rectus fascia. Bone anchor placement devices are often used to place bone anchors at selected insertion sites in the pubic bone. Sutures can then be attached to the bone anchors.

One type of bone anchor placement device suitable for installing a bone anchor in the pubic bone is a medical screwdriver. One known medical screwdriver is disclosed in U.S. Pat. No. 6,602,260 to Harari et al. The medical screwdriver of Harari et al. includes a body and a drive shaft that has an end that can drive a bone screw. A sleeve or sheath can be used to isolate the drive shaft from surrounding tissue. The sleeve is stationary and prevents the rotating shaft from injuring tissue surrounding a bone into which a screw is inserted. The sleeve includes a key that fits in a notch in the body of the screwdriver. In use, a surgeon connects the sleeve to the body of the screwdriver by aligning the key of the sleeve to the notch in the body of the screwdriver.

SUMMARY

The invention provides medical screwdrivers having a sleeve that can be coupled to the body of the medical screwdriver without the need to rotationally align the sleeve to the medical screwdriver. When coupled to the medical screwdriver, the sleeve resists rotation in at least one direction of rotation such as a driving direction of a drive shaft of the medical screwdriver, and functions to isolate the rotating drive shaft from surrounding tissue at a surgical site. A coupling in accordance with the invention between a sleeve and a medical screwdriver can provide multiple functional capabilities. First, such a coupling provides a physical connection between the sleeve and the medical screwdriver. Second, the coupling provides the capability to connect and disconnect the sleeve from the medical screwdriver. This provides for interchangeability between a single medical screwdriver and various sleeve configurations, which may be selected based on a particular surgical procedure or patient anatomy. Third, the coupling functions to position the sleeve with respect to the drive shaft of the medical screwdriver to isolate a portion of the drive shaft from tissue at a surgical site. Additionally, as noted above, the coupling allows the sleeve to be placed in connection with the medical screwdriver regardless of the rotational alignment of the sleeve to the medical screwdriver. Once connected, the sleeve resists rotation in at least one direction. Because of these features, medical screwdrivers in accordance with the invention can be quickly, easily, and reliably configured by a surgeon during a surgical procedure.

A medical screwdriver in accordance with one aspect of the invention comprises a body portion having a receiver, a drive shaft, a sleeve, and a coupling connecting the sleeve to the receiver. The sleeve surrounds at least a portion of the drive shaft when the sleeve is coupled to the receiver. The coupling comprises an end of the sleeve and the receiver of the body portion. The end of the sleeve and the receiver are designed so that the end of the sleeve can be coupled with the receiver without rotationally aligning the end of the sleeve to the receiver of the body portion. The end of the sleeve and the receiver are also designed so that when connected, the sleeve resists rotation in a rotational direction such as a drive direction of the drive shaft.

An exemplary coupling in accordance with the invention can include a sleeve having an end that has one or more raised portions, and a receiver having one or opposing surface such as a recessed region (e.g., groove, slot, or channel, for example) that can mate with and operatively cooperate with the one or more raised portions of the end of the sleeve when assembled to form the coupling. Alternately, positions of the raised portion and recessed region may be reversed, with the raised portion being present at the receiver and the recessed portion being present at the sleeve. An example is a coupled mechanism in the form of a one-way ratchet mechanism. Exemplary couplings can be designed so that a recessed region and a raised portion mechanically interfere to resist rotation of the sleeve in at least one direction, such as in a driving direction of the drive shaft. A recessed region and a raised portion can be designed to frictionally interfere with each other or can be designed to interfere by a hard stop. For example, a hard stop may include a surface portion of a recessed region that can contact a surface portion of a raised portion to impede rotation of the sleeve.

An aspect of the invention relates to a medical screwdriver that includes a body portion having a receiver; a drive shaft having first and second ends, the first end operatively connected to drive means associated with the body portion, the second end adapted to drive a medical screw; a sleeve surrounding at least a portion of the drive shaft; and a coupling comprising an end of the sleeve and the receiver of the body portion, wherein the end of the sleeve is adapted to be coupled with the receiver without rotationally aligning the end of the sleeve to the receiver, and wherein the coupling is adapted to prevent rotation of the sleeve in at least one direction.

In another aspect the invention relates to a medical screwdriver that includes a body portion; a drive shaft having first and second ends, the first end operatively connected to drive means associated with the body portion, the second end adapted to drive a medical screw; and a receiver at an end of the body portion, the receiver comprising a raised portion or a recessed region extending over a portion of a circumference of the receiver, the raised portion or recessed region exhibiting a variable height along the portion of circumference.

In another aspect the invention relates to a sleeve that includes a cylinder having first and second ends, an end comprising a raised portion or a recessed region over a portion of a circumference of the end, the raised portion or recessed region exhibiting a variable height along the portion of circumference.

Another aspect the invention relates to a method of inserting a medical screw at a surgical site. The method includes providing a medical screwdriver body and sleeve as described herein, coupling the end of the sleeve with the receiver of the body portion, and rotating the drive shaft in a driving direction to drive a medical screw, wherein the sleeve does not rotate with the drive shaft.

Another aspect of the invention relates to a combination of articles for use in a surgical procedure. The combination includes a medical screwdriver according to the present description, including a body and a sleeve, and a surgical implant.

BRIEF DESCRIPTION OF THE DRAWINGS

These and other features and aspects of the invention will become better understood with regard to the following description, appended claims, and accompanying drawings.

DETAILED DESCRIPTION

Figure 1:
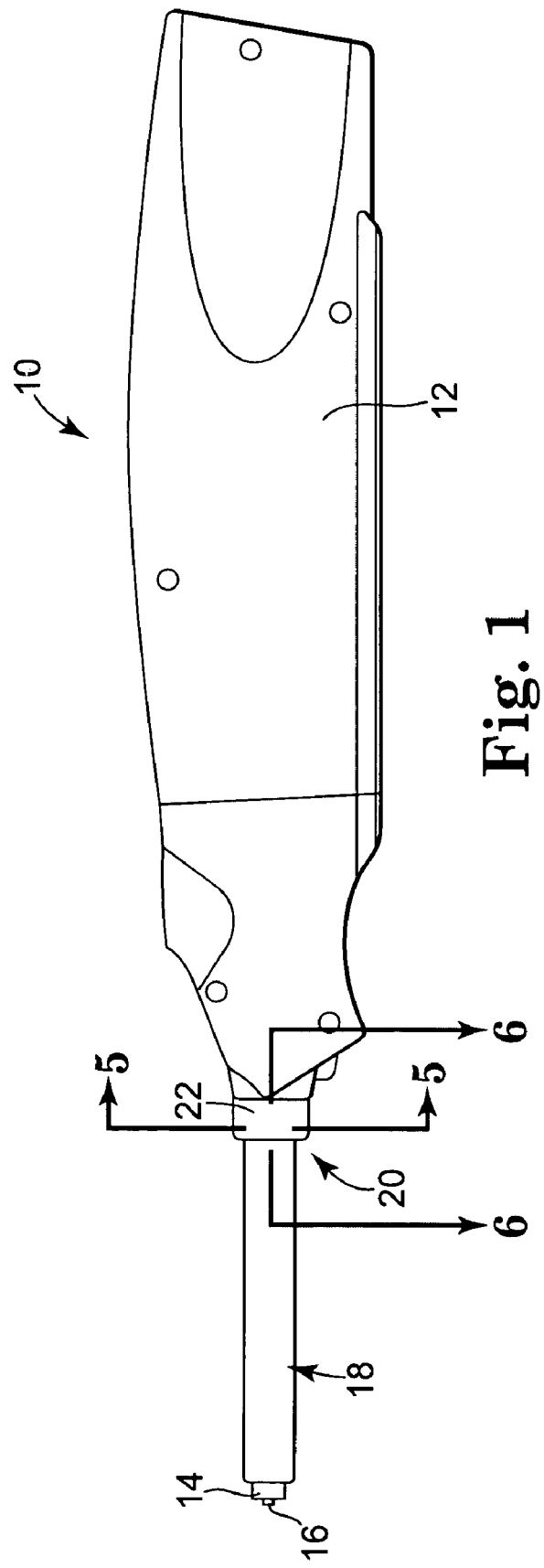
FIG. 1 is a side view of a medical screwdriver and sleeve in accordance with the invention having a coupling comprising a connecting end of the sleeve and a receiver of a body portion of the medical screwdriver.

A medical screwdriver as described herein includes a sleeve that covers a rotatable drive shaft of the medical screwdriver. In use, the sleeve prevents the rotating drive shaft from contacting body tissue at a surgical site.

A sleeve of the invention is prevented from rotating, e.g., in a drive direction of the drive shaft, when the shaft rotates. The sleeve is attached or coupled to a body portion of the medical screwdriver during a medical procedure. Certain prior medical screwdrivers allow for a sleeve to be uniquely aligned or otherwise keyed to the body of the medical screwdriver when attaching the sleeve to the body. Medical screwdrivers described herein do not require unique alignment between a sleeve and body of a medical screwdriver when attaching the sleeve to the body. A medical screwdriver in accordance with the invention includes a sleeve that can be coupled to a body portion of the medical screwdriver without requiring unique rotational alignment between the sleeve and the body portion. When coupled to the medical screwdriver, the sleeve also is prevented from rotating, e.g., in a direction of rotation of the drive shaft.

According to certain embodiments of the invention, coupling and anti-rotation features of the shaft can be provided by the use of a ratchet mechanism. Ratchet mechanisms are known and may take various forms including ratchet mechanisms that operate by use of a pawl that engages sloping surfaces of a solid or rotating structure such as a tooth or ramp structure of a wheel, bar, etc., permitting motion in one rotational direction only. Examples of such structures are described herein and others will be understood by those of skill in the mechanical arts. Any such ratchet may be useful for providing one-way rotational movement of a sleeve relative to a screwdriver body, when the sleeve and body are engaged as described herein.

According to certain specific embodiments, a body of a screwdriver includes a circular or cylindrical receiver near the base of the shaft to receive an end of a cylindrical sleeve. The receiver cooperates with the end of the sleeve in a way to provide features as described herein, including the ability to place the sleeve on the shaft and attach the sleeve to the screwdriver body without the need to circumferentially align the sleeve and the screwdriver body, and additionally the feature that the sleeve is prevented from rotating in a direction of rotation of the shaft. The features can be accomplished by various structures between the sleeve and the receiver, with particular examples of useful structures including certain specific ratcheting mechanisms based on structures of the sleeve and the receiver.

According to certain exemplary ratchet mechanisms, opposing surfaces of the sleeve and receiver can be in the form of raised portions and recessed regions generally located circumferentially over portions of opposing inner and outer circumferential surfaces of the receiver and the sleeve. A ratcheting effect can be achieved, for example, by having one or more opposing surfaces of raised portions and recessed regions exhibit progressively greater height along the portions of the circumferences (wherein "height" refers to the distance of a raised portion surface from an axial center of a cylindrical sleeve or receiver; and also refers to the distance of the surface of a recessed region from the axial center of a cylindrical sleeve or receiver, which may sometimes also be referred to as a "depth" of the recess). Exemplary embodiments of raised portions and recessed regions have surfaces that can be considered to be in the form of "bumps," "ramps," or "teeth," extending circumferentially around inner or outer surfaces of a sleeve or a receiver.

In general, ratcheting structures can include cooperative features at opposing surfaces of the receiver and the sleeve, including a recessed region (generally recessed relative to an inner or outer surface of a sleeve or receiver) and an opposing raised portion (generally extending from, or "raised," relative to an inner or outer surface of a sleeve or receiver). The recessed region may be part of either the sleeve or the receiver, as desired. Likewise, the opposing raised portion may be part of either the sleeve or the receiver, with a combination of sleeve and receiver including raised portions cooperatively opposed to recessed regions. In other words, in an opposing ratchet mechanism between a receiver and a sleeve, either of the sleeve or the receiver may include raised or "male" elements of the ratchet mechanism, with an opposing receiver or sleeve including recessed or "female" elements of the ratchet mechanism.

Additionally, a raised portion of either a sleeve or a receiver may be located at either an inner or outer surface of the sleeve or receiver, just as an opposing recessed region may be located at either an inner or an outer surface of the opposing receiver or sleeve. This means, for example, that the sleeve can fit inside of the receiver, or the sleeve may fit over the receiver, while according to either embodiment the raised portion could be either on the sleeve or the receiver with the opposing recessed region on the receiver or sleeve, respectively.

As just four possible configurations of opposing ratchet structures, an opposing sleeve and receiver may include: circumferential raised portions on the outside surface of a sleeve, opposing circumferential recessed regions at an inner surface of a receiver; circumferential raised portions on the inside surface of a sleeve, opposing circumferential recessed regions at an outer surface of a receiver; circumferential raised portions on the outside surface of a receiver, opposing circumferential recessed regions at an inner surface of a sleeve; and circumferential recessed regions on the outside surface of a sleeve, opposing circumferential raised portions at an inner surface of a receiver.

An exemplary medical screwdriver 10 is shown in FIG. 1. Medical screwdriver 10 comprises body portion 12 and drive shaft 14. Drive shaft 14 is controllably drivable by a battery-powered motor (not shown) that is located within body portion 12. Driving end 16 of drive shaft 14 is designed for driving a medical screw or the like (not shown). A medical screwdriver in accordance with the invention may comprise any drive means, known or future developed, capable of controllably driving a drive shaft for driving a medical screw or the like. Such drive means may include, for example, electric, kinematic, pneumatic, and hydraulic driving devices, as well as combinations thereof. A typical medical screwdriver is disclosed in U.S. Pat. No. 6,602,260 to Harari et al., the disclosure of which is fully incorporated herein by reference for all purposes.

Figure 2:
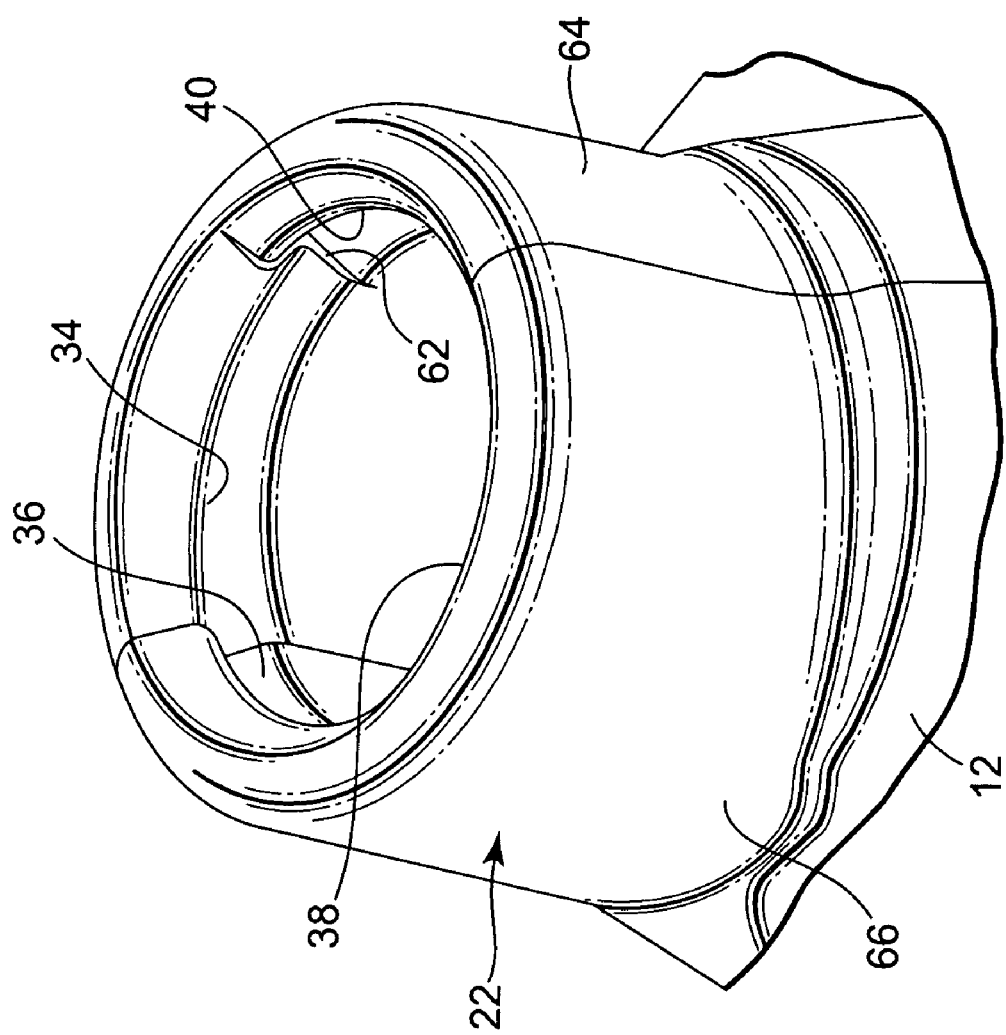
FIG. 2 is a perspective view of the receiver of the body portion of the medical screwdriver of FIG. 1.
Figure 3:
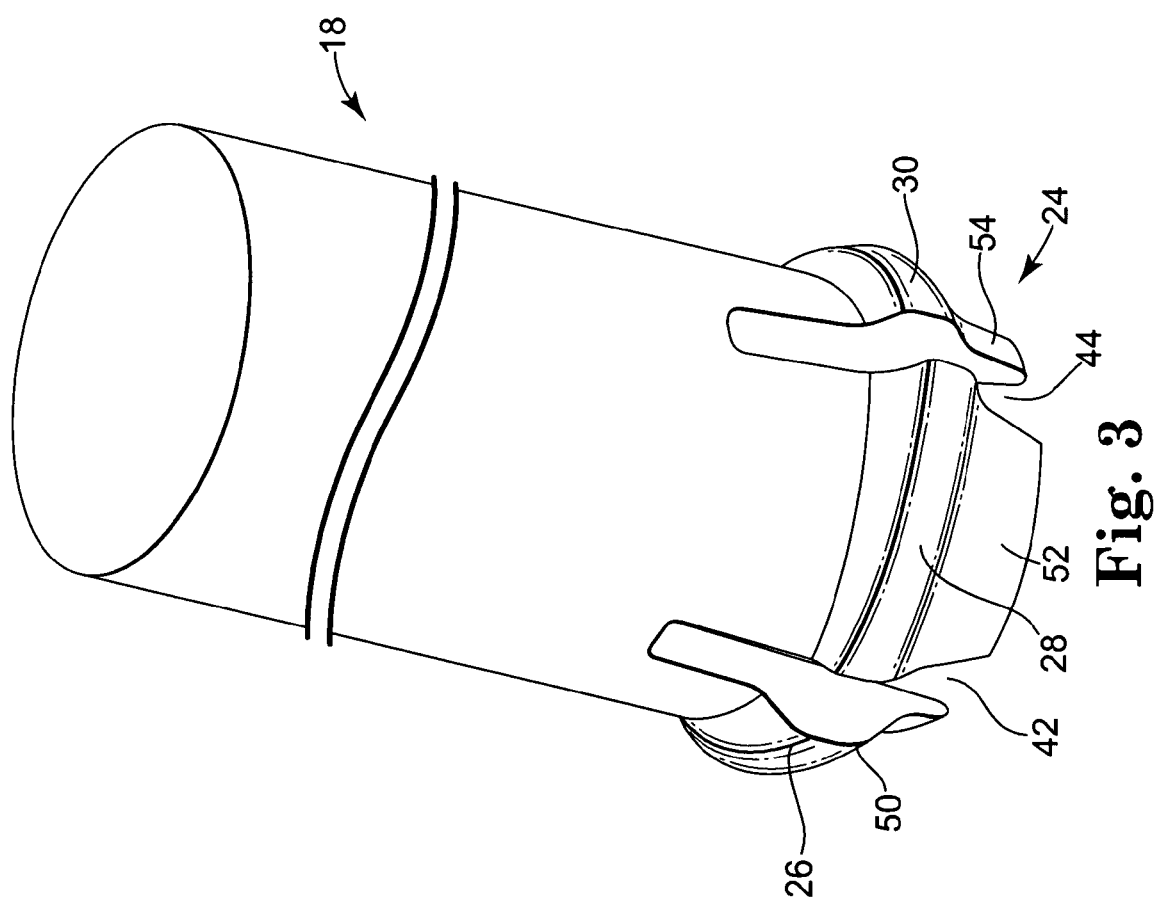
FIG. 3 is a perspective view of the sleeve of the medical screwdriver of FIG. 1.
Figure 4:
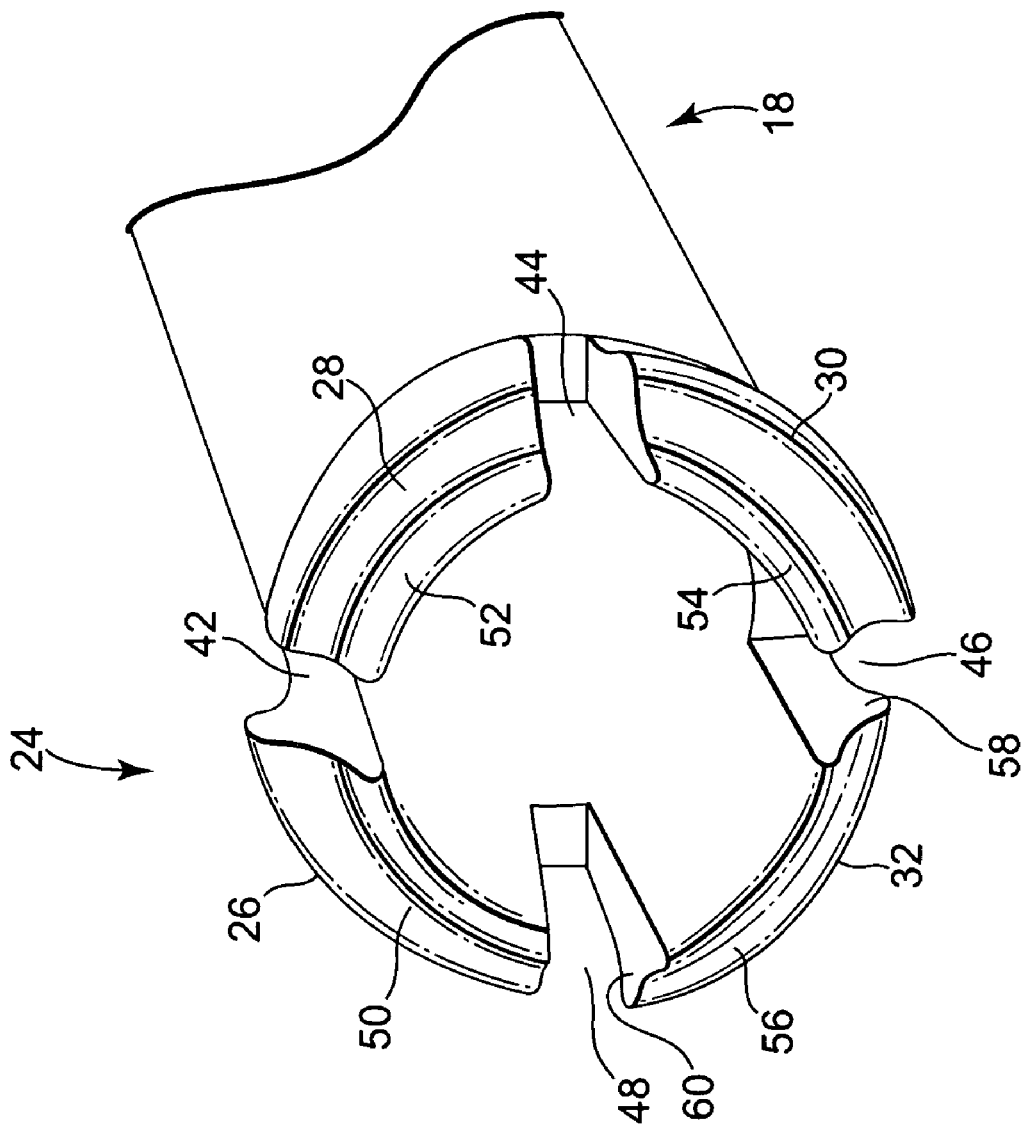
FIG. 4 is another perspective view of the sleeve of the medical screwdriver of FIG. 1, showing in particular the connecting end of the sleeve.
Figure 5:
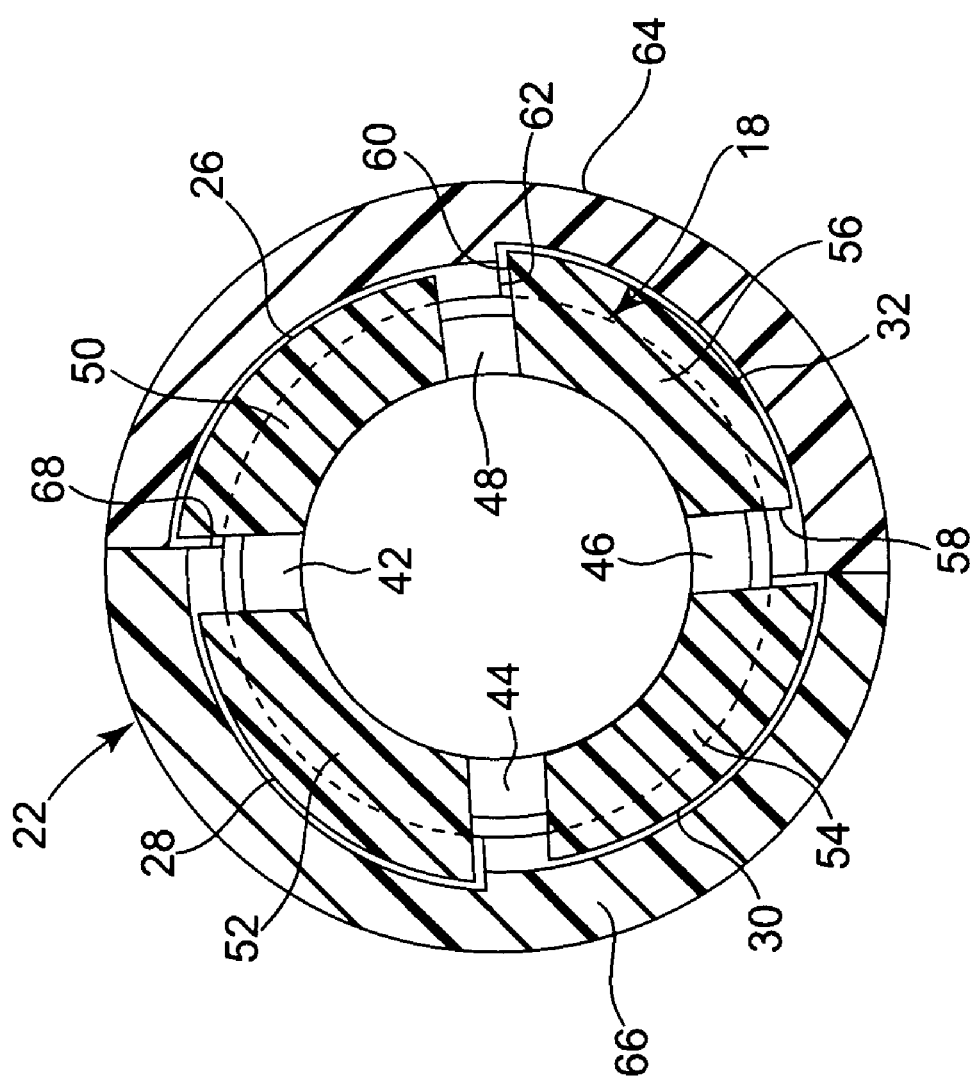
FIG. 5 is a cross-sectional view of the coupling of the medical screwdriver of FIG. 1, taken along the line 5-5.
Figure 6:
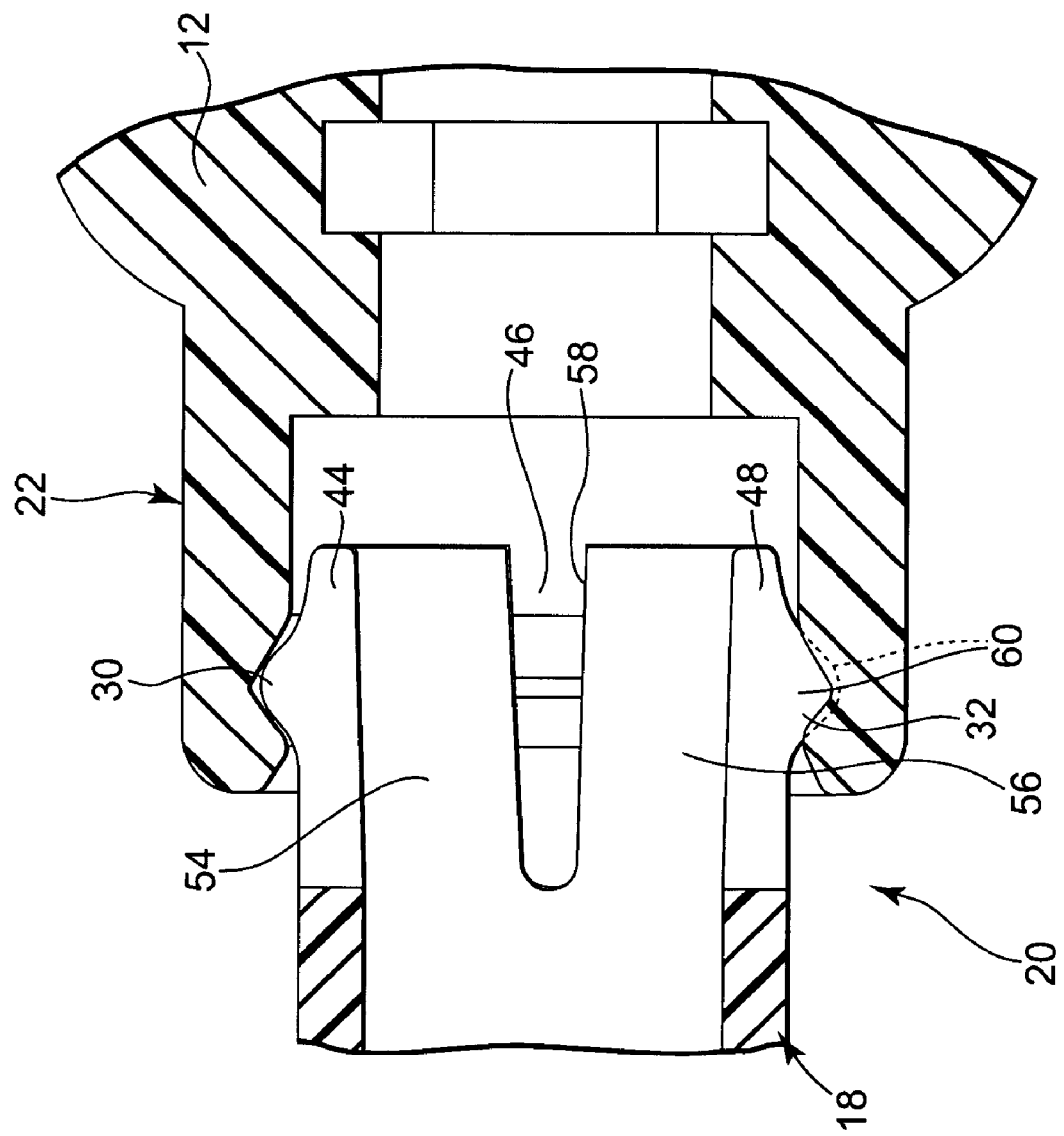
FIG. 6 is a cross-sectional view of the coupling of the medical screwdriver of FIG. 1, taken along the line 6-6.

Medical screwdriver 10, as illustrated, also includes sleeve 18 attached to body portion 12, at receiver 22, by coupling 20. Coupling 20 is made up of receiver 22 and connecting end 24 (not specifically illustrated in FIG. 1) of sleeve 18. Receiver 22 is illustrated in greater detail in FIG. 2 and connecting end 24 is shown in FIGS. 3 and 4. Additionally, cross-sectional views of coupling 20 are illustrated in FIGS. 5 and 6 and described in greater detail below.

Connecting end 24 of sleeve 18 is designed to be capable of being removably coupled with receiver 22. Referring to FIGS. 2-6 generally, connecting end 24 of sleeve 18 comprises distinct raised portions 26, 28, 30, and 32 designed to cooperatively engage with corresponding recessed regions 34, 36, 38, and 40 of receiver 22. As shown, raised portions 26, 28, 30, and 32 circumferentially extend around portions of an outside surface of connecting end 24, between first and second ends of each raised portion. Slits 42, 44, 46, and 48 extend lengthwise between ends of raised portions. Also as shown, each raised portion exhibits a progressively (circumferentially) increasing height, to form a ramp or tooth that increasingly extends outwardly from the outside surface of the sleeve between the first and second ends of each raised portion. Other possible embodiments of such raised portions, not illustrated, may have a variable height that does not form a ramp or a tooth; and raised portions that are present at the inner circumference of the sleeve.

Connecting end 24 of sleeve 18, as shown, comprises slits 42, 44, 46, and 48 that form an opening through the wall of sleeve 18 and extend longitudinally along a length of the sleeve. Slits 42, 44, 46, and 48 define end portions 50, 52, 54, and 56 of the connecting end 24 of the sleeve 18, which end portions, along with slits 42, 44, 46, and 48, structurally define raised portions 26, 28, 30, and 32, respectively. Slits 42, 44, 46, and 48 allow end portions 50, 52, 54, and 56 to flex inwardly during attachment of sleeve 18 to receiver 22. Slits 42, 44, 46, and 48, are illustrative, and useful slits may alternately be not exactly longitudinal (e.g., may slant along their lengths), or may be placed at positions other than the ends of raised portion (e.g., within a raised portion), if desired.

By designing coupling 20 as described, connecting end 24 of sleeve 18 can be coupled to receiver 22 of body portion 12 without requiring specific rotational alignment between connecting end 24 of sleeve 18 and receiver 24. End 24 of sleeve 18 can have any rotational alignment relative to receiver 22, and an effective operative union between sleeve 18 and body portion 12 (i.e., at the receiver of body portion 12) can be made as described further below. Slits 42, 44, 46, and 48 can allow end portions 50, 52, 54, and 56 to flex with respect to each other and with respect to the rest of sleeve 18. When connecting end 24 of sleeve 18 is pushed into receiver 22, end portions 50, 52, 54, and 56 can flex as needed to allow raised portions 26, 28, 30, and 32 to engage recessed regions 34, 36, 38, and 40 of receiver 22. That is, connecting end 24 is allowed to snap into engagement with receiver 22 due to the flexibility of end portions 50, 52, 54, and 56.

Sleeve 18 resists rotation in at least one direction, such as a direction of rotation of drive shaft 14, when sleeve 18 is coupled to body portion 12. Sleeve 18 is designed so that drive shaft 14 can functionally rotate within sleeve 18 with minimal resistance. Referring to cross-sectional views of coupling 20 in FIGS. 5 and 6, exemplary illustrated coupling 20 is designed to function as a ratchet mechanism. As shown, raised portion 32 of end portion 56 and slits 46 and 48 define free end 58 and interfering end 60 of raised portion 32. Receiver 22 includes wall portion 62 associated with recessed region 40 (see FIG. 2) that can cooperatively interfere with interfering end 60 of raised portion 32.

As shown, wall portion 62 is provided as part of an inside surface of body piece 64. It is contemplated, however, that wall portion 62 can be functionally provided in other ways such as by being defined by a mating surface of a body piece such as body piece 66. For example, body portion 12 of illustrated exemplary medical screwdriver 10 is formed from first and second body pieces, 64 and 66 respectively, assembled to form body portion 12. As shown, wall portion 68 is provided for cooperatively interfering with end portion 50, and is designed to function like wall portion 62 for cooperatively interfering with end portion 56.

Wall portion 62 is designed to engage with interfering end 60 of raised portion 32 when sleeve 18 rotates in a driving direction of drive shaft 14 (counter-clockwise rotation of sleeve 18 in FIG. 5) to prevent rotation of sleeve 18 in the direction of drive shaft 14. When sleeve 18 is rotated in the opposite direction (clockwise in FIG. 5), sleeve 18 may rotate against the ratchet mechanism. This configuration can be used for driving medical screws or the like with a right-handed thread into bone or tissue. Coupling 20 may also be designed for removing such screws or for driving screws that have a left-handed thread by reversing the configuration of coupling 20. In any case, raised portions 26, 28, and 30 may be similar to raised portion 32 and recessed regions 34, 36, and 40 may be similar to recessed region 38.

Connecting end 24 of sleeve 18, and receiver 22, do not need to be aligned in any specific or unique rotational manner to functionally couple sleeve 18 to body portion 12. Another aspect of this feature of coupling 20 can be explained with reference to the cross-sectional view of coupling 20 shown in FIGS. 5 and 6. In FIGS. 5 and 6, sleeve 18 is illustrated in a rotational position with respect to receiver 22, that restricts counter-clockwise rotation of sleeve 18 in receiver 22. This prevents sleeve 18 from rotating together with drive shaft 14 (not shown in FIGS. 5 and 6) during use. In the case where sleeve 18 is coupled to receiver 22 in a rotational orientation different from that shown in FIG. 5, a functional coupling will still be made and sleeve 18 can be rotated to rotationally position sleeve 18 in receiver 22 as shown in FIG. 5, to prevent further rotation in that direction. This could happen in use when drive shaft 14 rotates and frictionally drags sleeve 18 to seat in the position shown in FIG. 5 (with a surface of a raised portion in physical contact with a surface of a corresponding recessed region). Alternately, a surgeon may give sleeve 18 a partial counter-clockwise twist to position sleeve 18 as shown in FIG. 5 after sleeve 18 is initially installed. The degree of rotation needed will depend on the particular design of the coupling including the number of raised portions, end portions, ramps, or teeth, present at the end of a sleeve; the design of the raised portions and recessed regions; and the manner in which a raised portion and a recessed region interact to resist rotation in a particular direction. In any case, connecting end 24 of sleeve 18 and receiver 22 can be functionally coupled in any rotational alignment. An infinite number of rotational alignments between connecting end 24 of sleeve 18 and receiver 22 can be used to provide a functional coupling between connection end 24 of sleeve 18, and receiver 22.

Coupling 20 is exemplary and various modifications to the structure can be made in accordance with the invention. Moreover, coupling 20 can be adapted to any medical screwdriver, to attach a sleeve to cover at least a portion of a drive shaft. For example, the connecting end of the sleeve can be divided into any number of end portions, and slits can be provided in any way that allow the end portions to flex for connecting the sleeve to the receiver. The material for the sleeve can be any rigid material such as a plastic, having dimensions (size and shape) to fit over the shaft of a mechanical screwdriver, and having a useful wall thickness, e.g., a thickness that provides a desired flexibility to end portions for attaching to a receiver of a screwdriver body. Generally, cross-sectional profiles of raised portions of a sleeve and recessed regions of a receiver can have any desired shape capable of cooperatively mating together as described. The sleeve can be a rigid tubular structure formed as a single sleeve or formed from plural interconnected or otherwise assembled portions.

In use, a surgeon can attach an exemplary sleeve 18 to an exemplary body portion 12 of medical screwdriver 10 by simply pushing connection end 24 of sleeve 18 into receiver 22. This can be done manually. Advantageously, no special tools are needed to attach sleeve 18 to receiver 22. No unique rotational alignment between connecting end 24 of sleeve 18 and receiver 22 is required. This makes for easier and faster attachment of sleeve 18 to body portion 12. Medical screwdriver 10 can then be used to insert a medical screw into a bone or the like, such as during a procedure to treat urinary incontinence by installation of a urethral sling. Because of the design of coupling 20, sleeve 18 is prevented from rotating together with drive shaft 14 when the medical screw is implanted, and also isolates drive shaft 14 from tissue surrounding the implant site.

Medical screwdriver 10, including sleeve 18, can be provided together with a medical implant such as a sling for use in a procedure for treating urinary incontinence. The combination of medical screwdriver 10, sleeve 18, and medical implant can be packaged together, if desired, and supplied to a surgeon in that way. Preferably, medical screwdriver 10, sleeve 18, and medical implant are packaged in a sterile manner so that a surgeon can open the package and use medical screwdriver 10, sleeve 18, and the medical implant, during a medical procedure.

Other ways to make a coupling while still maintaining ease of use as described, could be to reverse portions of the design of the coupling, such as by placing cut features (i.e., slits) on receiver 22 (instead of sleeve 18) such that receiver 22 flexes and sleeve 18 is solid. Similarly, other configurations of raised portions 26, 28, 30, and 32, different from "ramps" or "teeth," could be useful to interface with recessed regions 34, 36, 38, and 40, to perform functions as described herein including the function of preventing rotation of the sleeve in at lease one direction.

The invention has been described with reference to certain exemplary embodiments. The foregoing description and examples have been given for clarity of understanding only. No unnecessary limitations are to be understood therefrom. It will be apparent to those skilled in the arts of mechanical screwdrivers and surgical instruments, that changes can be made to the exemplary embodiments described without departing from the scope of the invention.

What is claimed is:

1. A medical screwdriver comprising
    a body portion having a receiver,
    a drive shaft having first and second ends, the second end being adapted to drive a medical screw,
    a drive means for rotating the drive shaft, the drive means being disposed in the body portion and operatively connected to the first end of the drive shaft,
    a sleeve surrounding at least a portion of the drive shaft, and
    a coupling comprising an end of the sleeve and the receiver of the body portion, wherein the end of the sleeve is adapted to be coupled with the receiver without rotationally aligning the end of the sleeve to the receiver, wherein the end of the sleeve engages the receiver in a manner which prevents rotation of the sleeve during rotation of the drive shaft by the drive means, and wherein the coupling comprises a ratchet mechanism,
    wherein the end of the sleeve comprises a raised portion and the receiver comprises a recessed region adapted to cooperatively mate with the raised portion, wherein the raised portion and the recessed region cooperatively interfere to prevent rotation of the sleeve,
    wherein the raised portion is located over a portion of the circumference of the sleeve and exhibits a progressively greater height along the portion of circumference,
    wherein the end of the sleeve comprises at least one additional raised portion, the at least one additional raised portion located over a portion of the circumference of the sleeve and exhibiting a progressively greater height along the portion of circumference, and
    wherein the screwdriver comprises longitudinal slits at the end of the sleeve between adjacent ends of the raised portion and the at least one additional raised portion.

2. The medical screwdriver of claim 1, wherein the raised portion comprises a surface portion adapted to contact a surface portion of the recessed region to prevent rotation of the sleeve.

3. A method of inserting a medical screw at a surgical site, the method comprising:
    providing a medical screwdriver according to claim 1,
    coupling the end of the sleeve with the receiver of the body portion, and
    rotating the drive shaft in a driving direction to insert a medical screw.

4. A method according to claim 3 comprising placing a medical screw at tissue selected from bone and soft tissue.

5. A method according to claim 3 comprising placing a medical screw at soft tissue.

6. A method according to claim 3 comprising placing a medical screw at soft tissue selected from muscle, ligament, and fascia.

7. The method of claim 3, comprising anchoring a suture to a bone with the medical screw.

8. The method of claim 7, wherein the method is a surgical procedure to treat urinary incontinence.

9. A combination of articles for use in a surgical procedure, the combination comprising: a medical screwdriver according to claim 1, and a surgical implant.

10. The combination of claim 9, wherein the surgical implant is a urethral sling.

11. A medical screwdriver according to claim 1 wherein the drive means is capable of rotating the drive shaft without rotating the receiver.

12. A medical screwdriver according to claim 1 wherein
the sleeve comprises a proximal sleeve end, a distal sleeve end, and a length between the proximal sleeve end and the distal sleeve end,
the coupling comprises the proximal sleeve end and the receiver, and
the drive shaft enters the proximal end of the sleeve, extends through the length of the sleeve, and exits and extends beyond the distal end of the sleeve.

13. A medical screwdriver according to claim 12 wherein the drive means is capable of rotating the drive shaft without rotating the receiver.

14. A medical screwdriver according to claim 1 wherein
the body portion comprises a proximal body portion end and a distal body portion end,
the sleeve comprises a proximal sleeve end and a distal sleeve end,
the receiver is located proximate to the distal body portion end, and
the coupling comprises the proximal sleeve end engaging the receiver.

15. A medical screwdriver according to claim 14 wherein the drive means is capable of rotating the drive shaft without rotating the receiver.

16. A medical screwdriver comprising:
a body portion;
a drive shaft having first and second ends, the second end of the drive shaft adapted to drive a medical screw;
a receiver at an end of the body portion, the receiver comprising a fixed raised portion or a fixed recessed region extending over a portion of a circumference of the receiver, the raised portion or recessed region exhibiting variable height along the portion of circumference of the receiver; and
a sleeve capable of mating with and engaging the receiver in a manner which prevents rotation of the sleeve during rotation of the drive shaft, the sleeve comprising longitudinal slits at an end of the sleeve, wherein the sleeve isolates tissue from the drive shaft.

17. The medical screwdriver of claim 16, comprising a recessed portion that exhibits a progressively greater height along the portion of circumference.

18. The medical screwdriver of claim 16, wherein the raised or recessed region comprises multiple tooth structures around the circumference of the receiver.

19. The medical screwdriver of claim 16, wherein the receiver comprises a recessed region at an inner circumference of the receiver.

20. The medical screwdriver of claim 19, wherein the recessed region comprises multiple tooth structures.

21. A medical screwdriver according to claim 16 wherein
the sleeve comprises a proximal sleeve end, a distal sleeve end, and a length between the proximal sleeve end and the distal sleeve end,
the coupling comprises the proximal sleeve end engaging the receiver, and
the drive shaft enters the proximal end of the sleeve, extends through the length of the sleeve, and exits and extends beyond the distal end of the sleeve.

22. A medical screwdriver according to claim 21 wherein the drive shaft is capable of rotating without rotation of the coupling.

23. A medical screwdriver according to claim 16 wherein
the body portion comprises a proximal body portion end and a distal body portion end,
the sleeve comprises a proximal sleeve end and a distal sleeve end,
the receiver is located proximate to the distal body portion end, and
the coupling comprises the proximal sleeve end engaging the receiver.

24. A medical screwdriver according to claim 23 wherein the drive shaft is capable of rotating without rotation of the body portion.

25. A sleeve comprising:
a cylinder having a first end and a second end, the first end comprising longitudinal slits and an anti-rotation mechanism, the anti-rotation mechanism comprising a raised portion or a recessed region over a portion of a circumference between the longitudinal slits, the raised portion or recessed region exhibiting a variable height along the portion of circumference, the raised portion or recessed region comprising a ratchet tooth.

26. The sleeve of claim 25, comprising a raised portion exhibiting a progressively greater height along the portion of circumference.

27. The sleeve of claim 25, wherein the raised portion or recessed region comprises multiple tooth structures around the circumference of the receiver.

28. The sleeve of claim 25, wherein the sleeve comprises a raised portion at an outer circumference of the receiver.

29. The sleeve of claim 28, wherein the raised portion comprises multiple tooth structures.

* * * * *